United States Patent [19]

Erlich et al.

[11] Patent Number: 4,850,982

[45] Date of Patent: Jul. 25, 1989

[54] CATHETER

[76] Inventors: Brian H. Erlich; Frederick Erlich, both of 29540 Meadowlane Dr., Southfield, Mich. 48076

[21] Appl. No.: 155,060

[22] Filed: Feb. 11, 1988

Related U.S. Application Data

[63] Continuation-in-part of Ser. No. 23,813, Mar. 9, 1987, Pat. No. 4,772,275.

[51] Int. Cl.⁴ ............................................. A61M 25/00
[52] U.S. Cl. ........................................ 604/256; 604/96
[58] Field of Search .................................. 604/96–103, 604/256; 128/344

[56] References Cited

U.S. PATENT DOCUMENTS

| | | | |
|---|---|---|---|
| 2,819,718 | 1/1958 | Goldman | 604/96 |
| 3,331,371 | 7/1967 | Rocchi et al. | 604/256 X |
| 3,392,722 | 7/1968 | Jorgensen | 604/256 X |
| 4,166,468 | 9/1979 | Haynie | 604/256 X |
| 4,725,267 | 2/1988 | Vaillancourt | 604/192 |

Primary Examiner—Dalton L. Truluck
Attorney, Agent, or Firm—Arnold S. Weintraub; Gerald R. Black

[57] ABSTRACT

This new catheter minimizes the exposure of attendant personnel to contaminated materials. The catheter enables the withdrawal of the catheter from the patient and subsequent disposal thereof in a safe, easy to perform, and sanitary manner. The catheter includes a hollow tube made of a material that is inflatable and nonporous. A main passage is located within the tube and extends throughout the tube, from an open end of the tube and through an aperture located near a closed end of the tube. An inlet channel is attached to the tube and is in fluid communication with a chamber adjacent to the aperture. Prior to removing the catheter from the body of the patient, a fluid is injected through the channel and into the chamber, thereby inflating the inner surface wall of the tube, and essentially blocking the main passage. The closed chamber is secured to prevent the release of the injected fluid.

7 Claims, 1 Drawing Sheet

CATHETER

CROSS-REFERENCE TO RELATED APPLICATION

This is a continuation-in-part of copending application Ser. No. 023,813, filed on Mar. 9, 1987, the disclosure of which is hereby incorporated by reference, which is now U.S. Pat No. 4,772,275, and was issued on Sept. 20, 1988.

BACKGROUND OF THE INVENTION

1. Field of the Invention

This invention relates to the field of catheters which are used for injecting or withdrawing fluid into or from the body, and more particularly to a new design that enables a sanitary withdrawal of the catheter from the body of the patient and subsequent disposal thereof.

2. Background Art

Catheters are used for draining fluid from the body or injecting fluid into the body. The specific catheter design depends upon the particular use and particular body cavity involved. Catheters are used for a wide variety of applications: a urethral catheter is used to drain urine from the bladder, an intravenous catheter is used to feed fluid into the bloodstream, and an enema catheter introduces fluid into the gastro-intestinal tract.

U.S. Pat. No. 4,772,275 by Frederick L. Erlich, which was filed on Mar. 9, 1987, discloses a novel and unique design for the sterile containment and subsequent disposal of devices such as catheters, which have been in contact with body fluids. The invention involves a tubular sheath integral to the body fluid device, which encloses the device upon removal from the patient. The disclosure of this application is incorporated herein by reference.

All catheters are eventually removed from the body of the patient and disposed of. If the patient has a communicable or infectious disease, the catheter is most likely contaminated. Hence, the catheter must be carefully removed and disposed of to prevent contamination of attendant personnel and other persons. The problem of removing contaminated catheters is particularly acute in treating patients afflicted with highly infectious diseases, such as acquired immune deficiency syndrome (AIDS). For diseases such as AIDS, where the transmission mechanism is poorly understood, it is critical that all possible precautions are taken to protect attendant personnel. Of equal significance, personnel attending AIDS patients are apprehensive that they may be infected by the handling of contaminated catheters. This concern may interfere with the proper care and treatment afforded these patients.

Even in the absence of communicable diseases, it is unpleasant for the patient and others to be exposed to body fluids which are draining through the catheter during the removal of the catheter from the patient.

SUMMARY OF THE INVENTION

The present invention provides a new catheter design and removal method, which minimizes the exposure of attendant personnel to contaminated materials.

The present invention, also, provides a new catheter design and removal method, which enables the withdrawal of the catheter from the patient and subsequent disposal thereof in a safe, easy to perform, and sanitary manner.

The present invention provides a new catheter design, where the catheter includes a flexible hollow tube made of a material that is inflatable and nonporous. One end of the tube is open and the other end is closed. A main passage is located within the tube, and extends throughout the tube, from the open end of the tube to an aperture located near the closed end. An inlet channel is attached to the tube and is in fluid communication with a chamber adjacent to the aperture. Prior to removing the catheter from the body of the patient, a fluid is injected through the channel and into the chamber, expanding the chamber and inflating the inner surface wall of the tube, and essentially blocking the main passage. The closed chamber is secured to prevent the release of the injected fluid. A stiff segment may be positioned around the catheter at the location of the chamber in a snug manner. The stiff segment is made of a material which is more rigid than the tube material. The stiff segment restricts expansion of the outer surface wall, thereby enhancing internal expansion.

The catheter may also contain a rolled up, tubular sheath being disposed around the tube, the length of the sheath being sufficient to extend around the ends of the tube and allow enclosure thereof. As the catheter is withdrawn from the patient, the sheath is unrolled to its full length and extended around the contaminated catheter. The ends of the sheath may then be sealed and discarded.

For a more complete understanding of the present invention, reference is made to the following detailed description and accompanying drawings in which the presently preferred embodiments of the invention are illustrated by way of example. It is expressly understood, however, that the drawings are for purposes of illustration and description only, and are not intended as a definition of the limits of the invention. Throughout the following description and drawings, identical reference numbers refer to the same component throughout the several views.

DETAILED DESCRIPTION OF THE INVENTION

Figure 1:
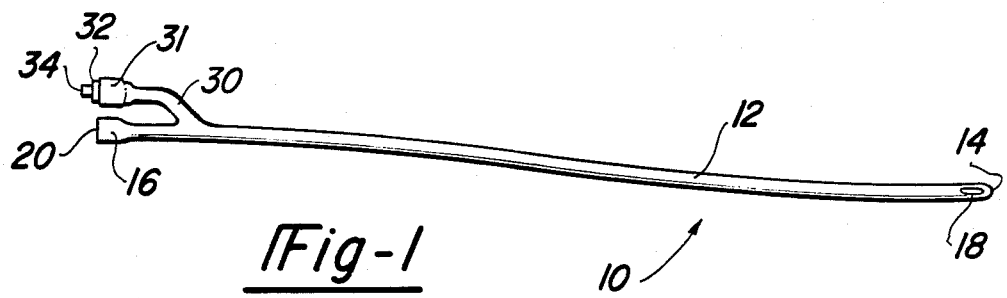
FIG. 1 is a perspective view of the catheter of the present invention.
Figure 4:
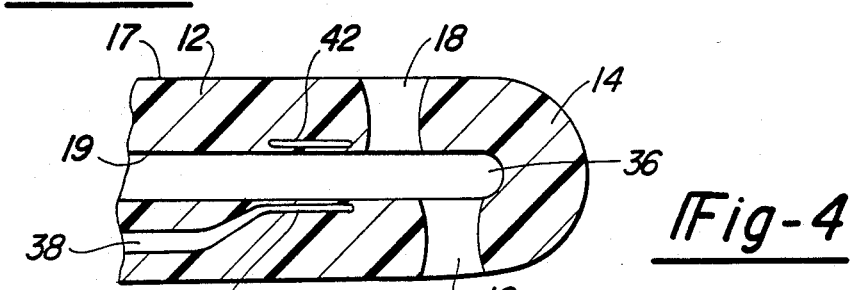
FIG. 4 is an exploded fragmentary section of the closed end of the catheter shown in FIG. 1 prior to inflation.

Referring now to the drawings, FIG. 1 shows a hollow and tubular catheter 10 of the present invention. Catheter 10 is formed of a nonporous, inflatable material, such as rubber, which is soft and nonirritating to the body. A flexible hollow tube 12 has one open end 16 and one closed end 14. A sealed device for collecting the fluid to be drained is attached to the open end 16 (not shown). FIG. 4 depicts an exploded fragmentary section of the closed end 14 shown in FIG. 1. A main passage 36 (see FIG. 4) is located within tube 12 and extends from an outlet 20 at open end 16 throughout tube 12, and to an aperture 18 located near closed end 14 (two apertures are shown in FIG. 4).

A branch 30 is a hollow extension which is integral to tube 12. An inner channel 38 extends from a branch 30 and is in fluid communication with an annular chamber 42, which surrounds passage 36 in a location adjacent to aperture 18. A hollow, rigid member 32 is shown partially inserted into the end of branch 30. Disposed within member 32 is a plug 34. An elastic sleeve 31 is fitted around branch 30 to hold rigid member 32 and plug 34 in place. Prior to the removal of catheter 10 from the body of the patient, plug 34 is removed and a fluid is injected through branch 30 by an air pump, or by some similar means. Chamber 42 expands causing inner surface wall 19 to inflate, thereby sealing main passage 36, and essentially blocking any fluid flow therein. A rigid plug 34 is then inserted into branch 30 to prevent the escape of fluid from channel 38 and any loss of pressure in chamber 42. Chamber 42 is located near inner wall 19 so that material resistance of wall 19 is minimized.

Figure 2:
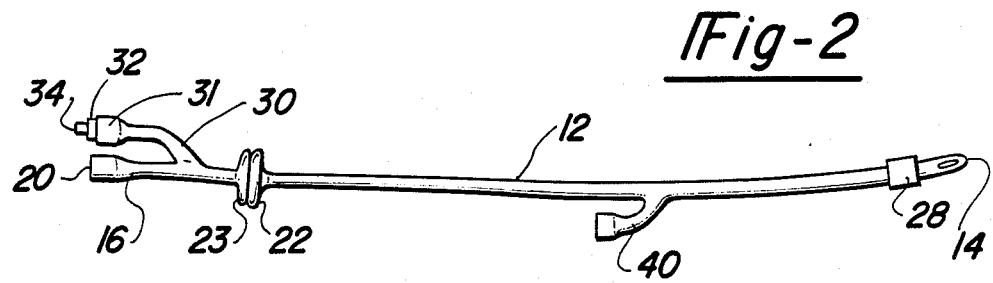
FIG. 2 is a perspective view of the preferred embodiment of the catheter of the present invention.

FIG. 2 depicts a perspective view of the preferred embodiment of the present invention. A stiff band segment 28 is snugly positioned around catheter 10 at the location of chamber 42. A material for band 28 is used which is more rigid than the material of flexible tube 12 but is still somewhat flexible. Band 28 must be somewhat elastic so that it can be positioned about tube 12, and form a snug fit therewith. Band 28 is made preferably of a rubber-type material. Band 28 strengthens hollow tube 12, so that any expansion caused by a pressure buildup within tube 12 will expand inwardly in the immediate area surrounded by band 28. By restricting the expansion of outer surface wall 17, the expansion of inner surface wall 19 is thereby enhanced. Any expansion of outer surface wall 17 during removal is to be minimized, since such expansion may impair such removal.

As disclosed in U.S. Pat. No. 4,772,275, closed end tubular sheath 22 is shown rolled up around tube 12. Sheath 22 is long enough that when it is unrolled it extends beyond closed end 14. Similarly, open end tubular sheath 23 is shown rolled up around tube 12, and is long enough that when it is unrolled it will extend beyond open end 20. Sheaths 22 and 23 are attached to tube 12 by a suitable material or bonding agent. The sheath is impervious to both liquids and gases and is flexible to enable rolling and unrolling. Typical sheath materials include polyethylene, polypropylene, and silicone elastomers.

Figure 3:
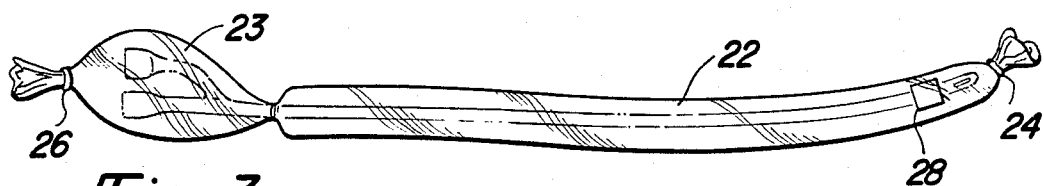
FIG. 3 is a perspective view of the embodiment of the catheter shown in FIG. 2 after it has been completely enclosed.

FIG. 3 depicts catheter 10 (the same embodiment as in FIG. 2) after it has been completely enclosed. Sheath 22 is secured as by sealing means 24, such as a paper-coated wire twist tie, and sheath 23 is similarly secured by sealing means 26. Alternately, the sheath may be unrolled and sealed as the catheter is withdrawn from the body. This method provides even stronger protection against contamination. Also, although two sheaths 22 and 23 are shown, one larger sheath can be used in a similar manner.

Figure 5:
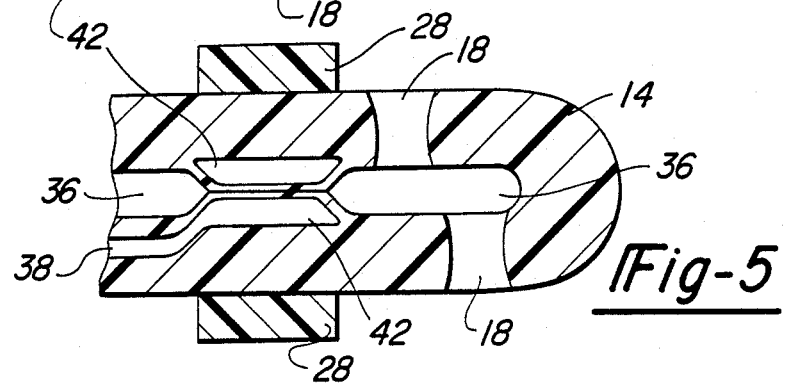
FIG. 5 is an exploded fragmentary section of the closed end of the catheter shown in FIG. 2 after inflation.

FIG. 5 depicts an exploded fragmentary section of closed end 14 after chamber 42 has expanded, thereby inflating inner wall 19. The position of band 28 is adjacent to aperture 18 and surrounds the expansion of inner wall 19.

Catheters designed for specific purposes may have additional features not shown in these drawings. Also, catheter size varies greatly depending upon the particular use.

While the invention has been described in conjunction with specific embodiments, it is evident that many alternatives, modifications, and variations will be apparent to those skilled in the art in light of the disclosure herein. It is intended that all such alternatives, modifications, and variations are included herein that fall within the spirit and scope of the appended claims.

We claim:

1. A catheter which is insertable into the body of a patient, the catheter comprising:
    (a) a tube having a wall made of an inflatable material, the tube having a first end and a second end, the tube wall having an outer surface, the tube having an aperture being disposed proximate to the second end, and the second end being insertable into the body of the patient;
    (b) a main passage being disposed within the tube, the passage extending substantially throughout the tube, the passage and the tube forming an inner surface wall that is coextensive with the tube, the passage extending from the first end to the aperture proximate to the second end, the passage enabling the transport of body fluids;
    (c) a chamber being disposed within the tube wall, the chamber being disposed between the aperture and the first end, the chamber being disposed nearer the inner wall than the outer wall; and
    (d) a channel having a first end and a second end, the channel being in fluid communication with the chamber at the second end, the channel being attachable to a supply of fluid at the first end and thereby enabling the fluid to be supplied into the chamber, thereby expanding the chamber, inflating the tube, and blocking the main passage.

2. The catheter of claim 1, further comprising:
    (d) a stiff segment which is positioned about the tube adjacent to the chamber, the stiff segment including a material which is more rigid than the inflatable material.

3. The catheter of claim 2, wherein the stiff segment is a band which is positioned around the outer surface wall of the tube in a snug manner.

4. The catheter of claim 1, further comprising:
    (d) a tubular sheath being disposed around the outer surface wall of the tube, the length of the sheath being sufficient to enclose the catheter.

5. A method of removing a catheter from the body of a patient, which comprises:
    (a) providing a catheter having a tube wall made of an inflatable material, the tube having a first end and a second end, the tube wall having an outer surface the tube having a main passage, the tube having an aperture disposed proximate to the second end and extending through the tube wall and into the main passage, the main passage and the tube forming an inner surface wall that is coextensive with the tube, the main passage extending from the first end to the aperture proximate to the second end, a chamber being disposed within the catheter, and a channel being in fluid communication with the chamber, the channel being in fluid communication with the chamber, the channel having a first end and a second end;
    (b) injecting a fluid through the first end of the channel and into the chamber, the injected fluid serving to expand the chamber, inflate the tube, and block the main passage; and (c) withdrawing the tube from the body of the patient.

6. The removal method of claim 5, further comprising:

(d) positioning a stiff segment between the first end and the aperture, the stiff segment comprising a material which is more rigid than the inflatable material, the stiff segment being placed in a snug manner around the outer surface wall of the tube.

7. A method of a sanitary disposal of a catheter, which comprises:

providing a catheter having a tube wall, the tube having a main passage extending therein with an open end and a closed end, the tube having an aperture located near the closed end, the tube being made of an inflatable material, the tube having an outer surface wall and an inner surface wall;

disposing a rolled-up sheath around the catheter, the sheath being long enough to enclose the catheter;

injecting a fluid into a chamber located within the tube, the injected fluid causing the chamber to expand and the inner surface to inflate until the main passage is blocked;

withdrawing the tube from the body of the patient; and enclosing the ends of the catheter with the sheath.

* * * * *